(12) United States Patent
Shimizu et al.

(10) Patent No.: US 12,387,838 B2
(45) Date of Patent: Aug. 12, 2025

(54) FAILED-IMAGE DECISION SUPPORT APPARATUS, FAILED-IMAGE DECISION SUPPORT SYSTEM, FAILED-IMAGE DECISION SUPPORT METHOD, AND COMPUTER READABLE STORAGE MEDIUM

(71) Applicant: KONICA MINOLTA, INC., Tokyo (JP)

(72) Inventors: Amai Shimizu, Hino (JP); Ryohei Ito, Hino (JP); Takuya Yamamura, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 490 days.

(21) Appl. No.: 17/704,423

(22) Filed: Mar. 25, 2022

(65) Prior Publication Data
US 2022/0328168 A1 Oct. 13, 2022

(30) Foreign Application Priority Data

Apr. 9, 2021 (JP) .................................. 2021-066191
Feb. 9, 2022 (JP) .................................. 2022-018432

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/10124* (2013.01); *G06T 2207/30008* (2013.01)

(58) Field of Classification Search
USPC ........................................................ 382/128
See application file for complete search history.

(56) References Cited

U.S. PATENT DOCUMENTS

2011/0144498 A1* 6/2011 Ando .................. A61B 8/463
600/443
2021/0065880 A1* 3/2021 Umezawa ............ G16H 30/40
(Continued)

FOREIGN PATENT DOCUMENTS

JP         2011255061 A    12/2011
WO      2020209290 A1    10/2020

OTHER PUBLICATIONS

Japanese Office Action (and an English language translation thereof) dated Jul. 8, 2025, issued in counterpart Japanese Application No. 2022-018432.

*Primary Examiner* — Jacky X Zheng
(74) *Attorney, Agent, or Firm* — Holtz, Holtz & Volek PC

(57) ABSTRACT

A failed-image decision support apparatus includes a hardware processor and an outputter. The hardware processor performs, among multiple types of failed-image determination processes, at least one failed-image determination process on a medical image, thereby generating a determination result and determination basis information indicating a basis for the determination result. The outputter outputs the determination result and the determination basis information. Another failed-image decision support apparatus includes a hardware processor. The hardware processor performs, among multiple types of failed-image determination processes, at least one failed-image determination process on a medical image, thereby generating a determination result and determination basis information indicating a basis for the determination result, and controls output of the determination result and the determination basis information.

17 Claims, 13 Drawing Sheets

(56) References Cited

U.S. PATENT DOCUMENTS

2022/0028075 A1 1/2022 Sugahara
2022/0058800 A1* 2/2022 Ito .......................... A61B 6/586

* cited by examiner

FAILED-IMAGE DECISION SUPPORT APPARATUS, FAILED-IMAGE DECISION SUPPORT SYSTEM, FAILED-IMAGE DECISION SUPPORT METHOD, AND COMPUTER READABLE STORAGE MEDIUM

CROSS-REFERENCE TO RELATED APPLICATIONS

The entire disclosure of Japanese Patent Applications No. 2021-066191 filed Apr. 9, 2021 and No. 2022-018432 filed Feb. 9, 2022 are incorporated herein by reference in their entirety.

BACKGROUND

Technological Field

The present disclosure relates to a failed-image decision support apparatus, a failed-image decision support system, a failed-image decision support method, and a computer readable storage medium.

Description of the Related Art

There has been known a technology for determining whether imaging for a medical image has failed (whether a medical image is a failed image).

For example, in JP 2011-255061 A, there is disclosed a positioning determination apparatus that determines whether a radiograph of a specific part is an image obtained by imaging with appropriate positioning, extracts predetermined feature amounts from image data of a specific region of the radiograph, and determines whether a part of the specific part is missing on the basis of learning results of the feature amounts by a predetermined learning algorithm.

SUMMARY

There are not only positioning but also various standpoints for determining whether medical images are failed images. Hence, it is assumed that multiple types of failed-image determination processes are performed on a single image. In such a case, even when the determination result as to whether the image is a failed image and the image itself are displayed, which is disclosed in JP 2011-255061 A, the user does not know the basis for the determination result, such as which failed-image determination process has been used or for what reason the image has been determined as a failed image. Hence, it is hard for the user to accept the determination result.

The present disclosure has been made in view of the above problems, and objects thereof include improving user's satisfaction with determination results of failed-image determination processes.

In order to achieve at least one of the objects, according to a first aspect of the present disclosure, there is provided a failed-image decision support apparatus including:
  a hardware processor that performs, among multiple types of failed-image determination processes, at least one failed-image determination process on a medical image, thereby generating a determination result and determination basis information indicating a basis for the determination result; and
  an outputter that outputs the determination result and the determination basis information.

In order to achieve at least one of the objects, according to a second aspect of the present disclosure, there is provided a failed-image decision support apparatus including a hardware processor that:
  performs, among multiple types of failed-image determination processes, at least one failed-image determination process on a medical image, thereby generating a determination result and determination basis information indicating a basis for the determination result; and
  controls output of the determination result and the determination basis information.

In order to achieve at least one of the objects, according to a third aspect of the present disclosure, there is provided a failed-image decision support system including:
  a hardware processor that performs, among multiple types of failed-image determination processes, at least one failed-image determination process on a medical image, thereby generating a determination result and determination basis information indicating a basis for the determination result; and
  an outputter that outputs the determination result and the determination basis information.

In order to achieve at least one of the objects, according to a fourth aspect of the present disclosure, there is provided a failed-image decision support system including a hardware processor that:
  performs, among multiple types of failed-image determination processes, at least one failed-image determination process on a medical image, thereby generating a determination result and determination basis information indicating a basis for the determination result; and
  controls output of the determination result and the determination basis information.

In order to achieve at least one of the objects, according to a fifth aspect of the present disclosure, there is provided a failed-image decision support method including:
  performing, among multiple types of failed-image determination processes, at least one failed-image determination process on a medical image, thereby generating a determination result and determination basis information indicating a basis for the determination result; and
  outputting the determination result and the determination basis information.

In order to achieve at least one of the objects, according to a sixth aspect of the present disclosure, there is provided a failed-image decision support method including:
  performing, among multiple types of failed-image determination processes, at least one failed-image determination process on a medical image, thereby generating a determination result and determination basis information indicating a basis for the determination result; and
  controlling output of the determination result and the determination basis information.

In order to achieve at least one of the objects, according to a seventh aspect of the present disclosure, there is provided a non-transitory computer readable storage medium storing a program that causes a computer to:
  perform, among multiple types of failed-image determination processes, at least one failed-image determination process on a medical image, thereby generating a determination result and determination basis information indicating a basis for the determination result; and
  output the determination result and the determination basis information.

In order to achieve at least one of the objects, according to an eighth aspect of the present disclosure, there is provided a non-transitory computer readable storage medium storing a program that causes a computer to:

perform, among multiple types of failed-image determination processes, at least one failed-image determination process on a medical image, thereby generating a determination result and determination basis information indicating a basis for the determination result; and control output of the determination result and the determination basis information.

BRIEF DESCRIPTION OF THE DRAWINGS

The objects, advantages, and characteristics provided by one or more embodiments of the present invention will become more fully understood from the detailed description given hereinbelow and the appended drawings that are given by way of illustration only, and thus are not intended as a definition of the limits of the present invention, wherein:

FIG. 7 shows an example of the switching button that toggles the marker as the region indicator shown in FIG. 4 between ON and OFF;

FIG. 8 shows an example of the switching button that toggles the marker as the region indicator shown in FIG. 4 between ON and OFF;

FIG. 9 shows an example of the switching button that toggles the marker as the region indicator shown in FIG. 4 between ON and OFF;

FIG. 10 shows display examples of an alert;

FIG. 13 is a display example of a target image;

DETAILED DESCRIPTION OF EMBODIMENTS

Hereinafter, one or more embodiments of the present disclosure will be described in detail with reference to the drawings. However, the scope of the present invention is not limited to the embodiments or illustrated examples.

<1. Radiographic System>

First, configuration of a radiographic system (hereinafter "system 100") according to an embodiment(s) will be described.

Figure 1:
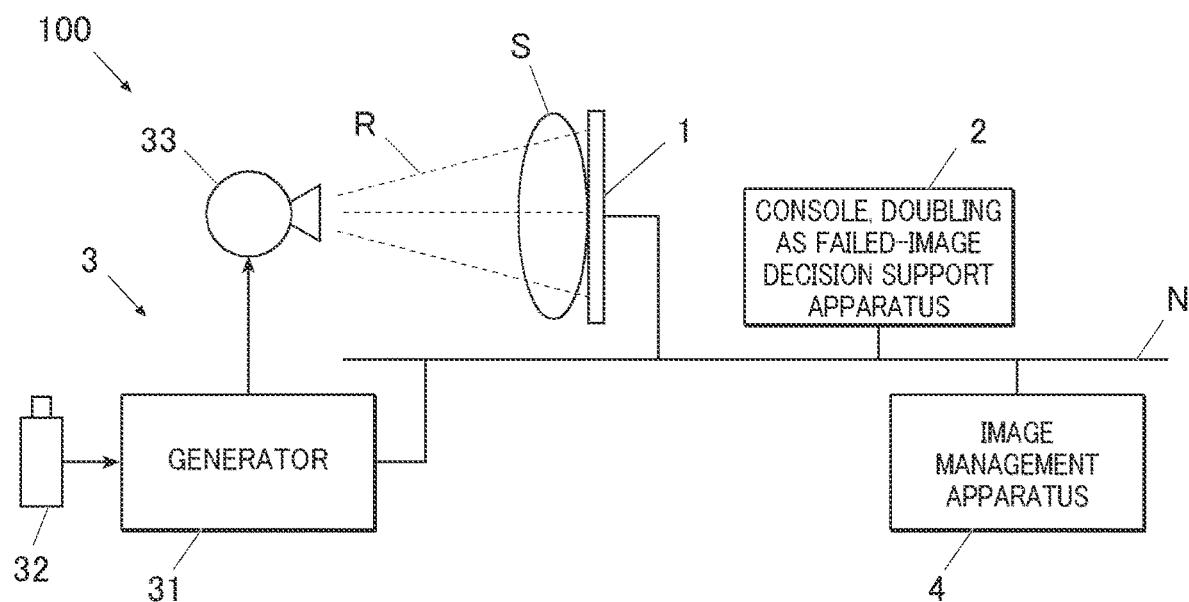
FIG. 1 is a block diagram showing an example of a radiographic system according to an embodiment(s) of the present disclosure.

FIG. 1 is a block diagram of the system 100.

As shown in FIG. 1, the system 100 includes a radiographic imaging apparatus (hereinafter "imaging apparatus 1") and a console 2.

The system 100 of this embodiment further includes a radiation emission apparatus (hereinafter "emission apparatus 3") and an image management apparatus 4.

These apparatuses 1 to 4 can communicate with one another, for example, via a communication network N (LAN (Local Area Network), WAN (Wide Area Network), Internet, etc.).

The system 100 may be fixed in an imaging room or may be configured to be movable/portable (e.g., visiting cart).

The system 100 may be capable of communicating with a not-shown hospital information system (HIS), a not-shown radiology information system (RIS) and so forth.

[1-1. Radiation Emission Apparatus]

The emission apparatus 3 includes a generator 31, an emission instructing switch 32 and a radiation source 33.

In response to an operation on the emission instructing switch 32, the generator 31 applies, to the radiation source 33 (tube), a voltage suitable for preset imaging conditions.

When the generator 31 applies the voltage to the radiation source 33, the radiation source 33 generates a dose of radiation R (e.g., X-rays) corresponding to the applied voltage.

The emission apparatus 3 of this embodiment emits radiation R in a mode suitable for the form of radiographs (still images or dynamic images each formed of a plurality of frames) to be generated.

In the case of still images, the emission apparatus 3 emits radiation R once per press on the emission instructing switch 32.

In the case of dynamic images, the emission apparatus 3 repeats emission of pulsed radiation R multiple times per predetermined time (e.g., 15 times per second) or keeps emitting radiation R for a predetermined time, per press on the emission instructing switch 32.

[1-2. Radiographic Imaging Apparatus]

The imaging apparatus 1 generates digital data of radiographs where the imaging part of a subject S is captured.

The imaging apparatus 1 is a portable FPD (Flat Panel Detector).

More specifically, although not shown, the imaging apparatus 1 of this embodiment includes a sensor substrate, a scanner, a reader, a controller and a communication unit. On the sensor substrate, imaging elements and switching elements are arranged two-dimensionally (in a matrix). The imaging elements generate electric charges corresponding to the dose of the radiation R received. The switching elements accumulate and release the electric charges. The scanner turns on and off each switching element. The reader reads the amounts of the electric charges released from respective pixels as signal values. The controller controls the components of the imaging apparatus 1, and generates radiographs from the signal values read by the reader. The communication unit sends data of the radiographs generated, various signals and so forth to other apparatuses (console 2, emission apparatus 3, image management apparatus 4, etc.), and receives various pieces of information and various signals from the other apparatuses.

The imaging apparatus 1 generates image data of still images (hereinafter "still image data") or image data of dynamic images (hereinafter "dynamic image data") by accumulating and releasing electric charges and reading these as signal values in sync with the timing when the emission apparatus 3 emits radiation R.

In the case of generating still image data, the imaging apparatus 1 generates a radiograph per press on the emission instructing switch 32.

In the case of generating dynamic image data, the imaging apparatus 1 generates frames of a dynamic image per predetermined time (e.g., 15 frames per second) per press on the emission instructing switch 32.

The imaging apparatus 1 may be integrated with the emission apparatus 3.

[1-3. Console]

The console 2 sets various imaging conditions in at least one of the imaging apparatus 1 and the emission apparatus 3.

The console 2 is configured by a PC, a dedicated apparatus or the like.

The imaging conditions include conditions about the subject S (part/site of the body to be imaged (imaging part), imaging direction, body build, etc.), conditions about emission of radiation R (tube voltage, tube current, emission time, current-time product (mAs value), etc.), and conditions about image reading by the imaging apparatus 1.

The console 2 may automatically set the imaging conditions on the basis of examination order information obtained from another system (HIS, RIS, etc.) or may set these on the basis of operations made by a user (e.g., technician) on/with an operation unit 25 (under manual operations).

The console 2 of this embodiment doubles as a failed-image decision support apparatus.

In other words, the console 2 has a function to assist the user in deciding whether radiographs are failed images (i.e., in making failed-image decision).

When imaging for a radiograph fails and re-imaging is performed, a mark (flag in this embodiment) is attached to the radiograph decided as a "failed image" so that the failed radiograph is not used for diagnosis.

Details of the console 2 will be described later.

[1-4. Image Management Apparatus]

The image management apparatus 4 manages image data generated by the imaging apparatus 1.

The image management apparatus 4 is a picture archiving and communication system (PACS), an image diagnosis workstation (IWS) or the like.

<2. Details of Console>

Next, the console 2 having a function of a failed-image decision support apparatus will be described in detail.

Figure 2:
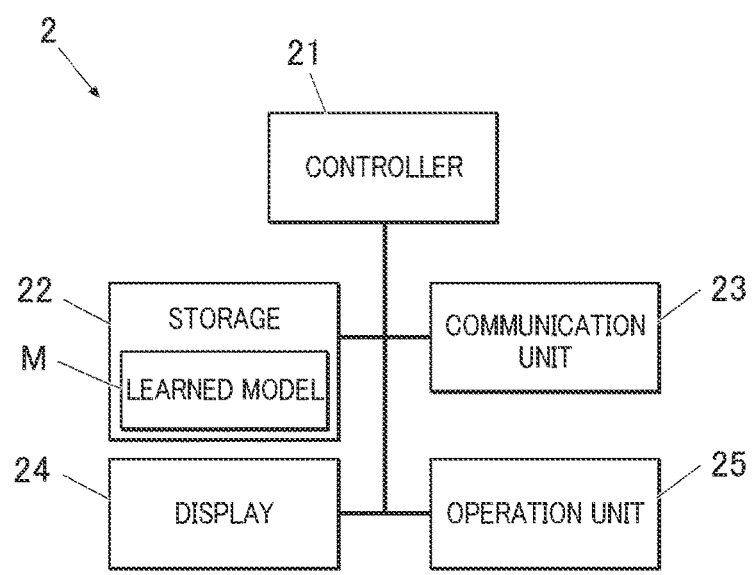
FIG. 2 is a block diagram showing a functional configuration of a console shown in FIG. 1.
Figure 3:
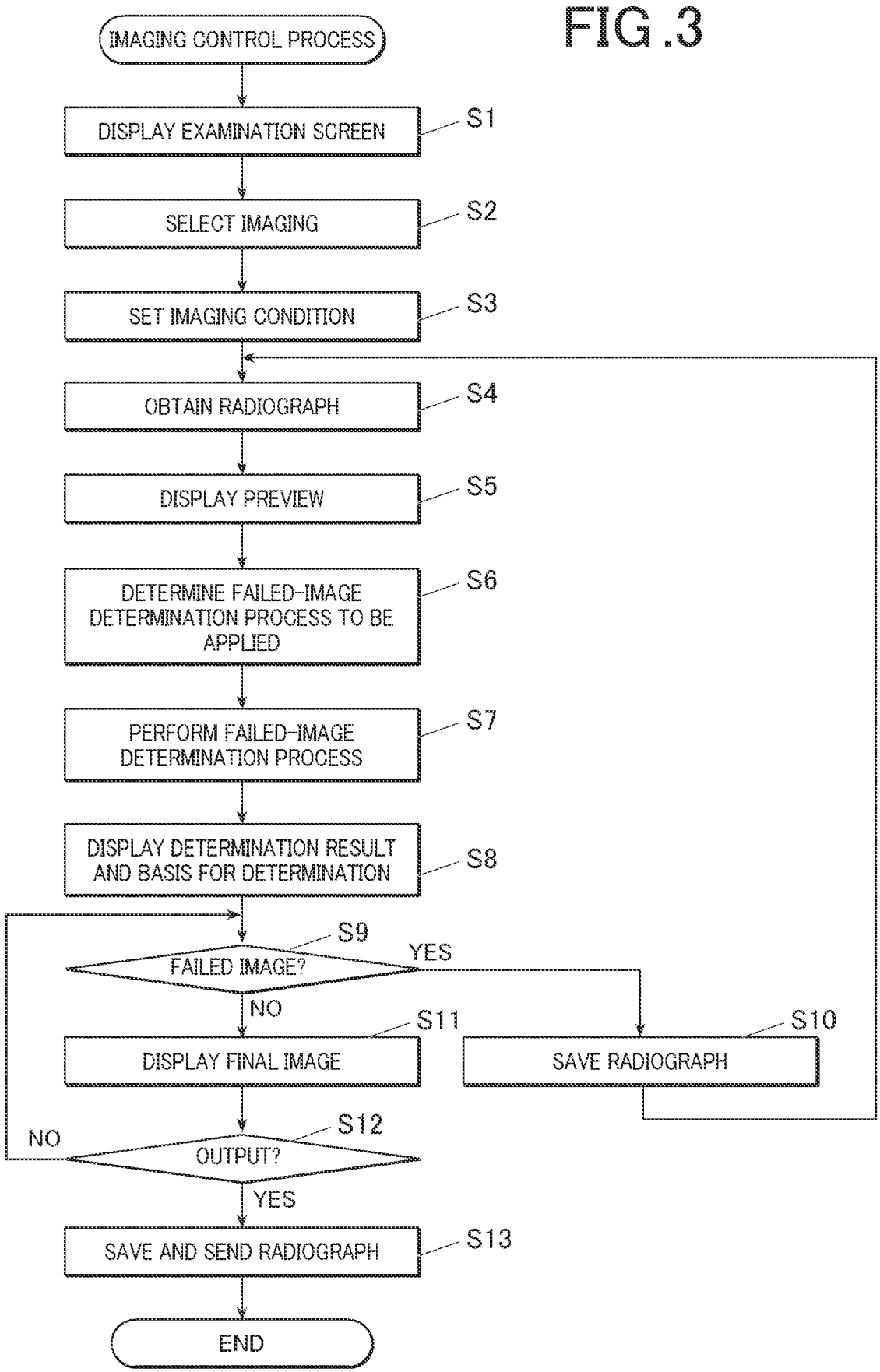
FIG. 3 is a flowchart of an imaging control process that is performed by a controller shown in FIG. 2.

FIG. 2 is a block diagram showing a functional configuration of the console 2. FIG. 3 is a flowchart of a process in the console 2.

[2-1. Configuration of Console]

As shown in FIG. 2, the console 2 includes a controller 21 (hardware processor), a storage 22, a communication unit 23, a display 24 and an operation unit 25. These components 21 to 25 are electrically connected to one another by a bus or the like.

The controller 21 includes a CPU (Central Processing Unit), a RAM (Random Access Memory) and a ROM (Read Only Memory).

The ROM stores various programs that are executed by the CPU, parameters necessary for the execution of the programs, and so forth.

The CPU reads the various programs stored in the ROM, loads them to the RAM, performs various processes in accordance with the loaded programs, and performs centralized control of operation of the components of the console 2.

The storage 22 is configured by a nonvolatile memory, a hard disk and/or the like.

The storage 22 is capable of storing image data of radiographs obtained from other apparatuses (imaging apparatus 1, image management apparatus 4, etc.). For example, the storage 22 stores each radiograph associated with a flag indicating whether the radiograph is a failed image, a determination result(s) of a failed-image determination process(es) performed thereon, information indicating the basis/bases for the determination result(s) (determination basis information), part (or imaging-part) information, technician-in-charge information, and so forth.

The storage 22 of this embodiment further stores learned models M.

The learned models M correspond to respective types of failed-image determination processes that can be performed by the console 2. The learned models M have been generated by machine learning (e.g., deep learning) using image data of radiographs and correct determination results (correct labels) as to whether the image data are failed images.

Then, when image data of radiographs are input to their corresponding learned models M, the learned models M infer and output analysis results, which will be described in detail later.

The learned models M may have been generated by machine learning using, in addition to the image data and the correct labels, information on coordinates of the position of the subject S in each radiograph. This can improve accuracy of analysis results.

Types of failed-image determination processes (algorithms for failed-image determination processes) to be applied to radiographs are different from imaging part to imaging part and from imaging direction to imaging direction.

For example, when the imaging part is a joint (knee joint, elbow joint, ankle joint, etc.), at least one of failed-image determination processes about positioning (misalignment between the lateral condyle and the medial condyle), wrong-side part and wrong part is performed.

When the imaging part is a limb (arm or leg), at least one of failed-image determination processes about wrong-side part and wrong part is performed.

When the imaging part is a part of the trunk (abdomen, spine, hip joint or the like), at least one of failed-image determination processes about saturation due to excessive dose, body motion and wrong part is performed.

When the imaging part is the chest, at least one of failed-image determination processes about lung lack and wrong part is performed.

The storage 22 stores, for each combination of the imaging part and the imaging direction, information indicating the type(s) of a failed-image determination process(es) (e.g., name(s) of an algorithm(s) therefor) to be performed on radiographs of the combination and a learned model(s) M to be used in the failed-image determination process(es), associated with the combination. Depending on the imaging part, metal may be embedded therein. For such imaging part, failed-image determination processes for the case of presence of metal and the case of absence of metal are prepared. The storage 22 stores, for each combination of such imaging part, the imaging direction and presence/absence of metal, information indicating the type(s) of a failed-image determination process(es) to be performed on radiographs that come under the conditions (i.e., of the combination) and a learned model(s) M to be used in the failed-image determination process(es), associated with the combination.

The storage 22 further stores examination order information sent from the RIS or the like.

The communication unit 23 is configured by a communication module or the like.

The communication unit 23 sends and receives various signals and various data to and from other apparatuses (imaging apparatus 1, emission apparatus 3, image management apparatus 4, etc.) connected thereto via the communication network N with wires or wirelessly.

The display 24 is configured by an LCD (Liquid Crystal Display), a CRT (Cathode Ray Tube) or the like. The display 24 displays radiographs and so forth in accordance with image signals received from the controller 21.

The operation unit 25 includes a keyboard (cursor keys, numeric input keys, various function keys, etc.), a pointing device (a mouse, etc.) and a touchscreen overlaid on the surface of the display 24. The operation unit 25 outputs, to the controller 21, control signals corresponding to operations made by the user.

The console 2 may not include the display 24 and the operation unit 25, and may receive control signals from an input apparatus provided separately from the console 2 and output image signals to a display apparatus (monitor) provided separately from the console 2 via the communication unit 23 or the like, for example.

If another apparatus(es) (image management apparatus 4, etc.) includes a display and an operation unit, the console 2 may receive control signals from the operation unit of another apparatus and output image signals to the display of the/another apparatus (or may share a display and an operation unit with another apparatus(es)).

[2-2. Operation of Console]

Next, operation of the console 2 will be described with reference to FIG. 3.

The console 2 performs an imaging control process shown in FIG. 3. The imaging control process is performed by the CPU of the controller 21 working together with a program stored in the ROM of the controller 21 when, for example, examination order information is selected with the operation unit 25 from an examination list screen displayed by the display 24.

The controller 21 first causes the display 24 to display an examination screen 241 about selected examination order information (Step S1).

The examination screen 241 (shown, for example, in FIG. 4) includes imaging selection buttons 241a each of which shows imaging contents (imaging part, imaging direction, etc.) included in examination order information, a setting area 241b where image reading conditions and image processing conditions are set for selected imaging, an image display area 241c where a radiograph obtained by selected imaging is displayed, a reject button 241d, and an output button 241e. In Step S1, no radiograph is displayed in the image display area 241c.

When an imaging selection button 241a is pressed with the operation unit 25 to select imaging (imaging part, imaging direction) to be performed (Step S2), the controller 21 sets imaging conditions (image reading conditions and radiation emission conditions) in the imaging apparatus 1 and the emission apparatus 3 (Step S3).

For example, on the basis of the imaging part, the imaging direction and so forth indicated by the pressed imaging selection button 241a, the controller 21 automatically sets imaging conditions (image reading conditions exemplified by pixel size, image size, frame rate, etc.) in the imaging apparatus 1, and sets imaging conditions (radiation emission conditions exemplified by tube voltage (kV), tube current (mA), emission time (ms), etc. of a radiation source) in the emission apparatus 3. Alternatively, in response to operations made by the user on the examination screen 241 with the operation unit 25, the controller 21 may set, in the imaging apparatus 1, imaging conditions (image reading conditions) for imaging to be performed. As to radiation emission conditions, the user may set them with an operation panel of the emission apparatus 3.

After an imaging selection button 241a is pressed, and imaging conditions are set, the user (technician) places the subject S between the radiation source 33 of the emission apparatus 3 and the imaging apparatus 1, thereby performing positioning.

When the user operates the emission instructing switch 32, the emission apparatus 3 emits radiation R to the imaging part of the subject S, namely, irradiates the imaging part of the subject S with radiation R.

The imaging apparatus 1 generates a radiograph (a still image or frames of a dynamic image) in which the imaging part is captured, at the timing(s) when the imaging apparatus 1 receives the radiation R from the emission apparatus 3, and sends its image data (still image data or dynamic image data) to the console 2.

When the controller 21 of the console 2 receives (obtains) the image data of the radiograph via the communication unit 23 (Step S4), the controller 21 causes the display 24 to display a preview of the received radiograph in the image display area 241c of the examination screen 241 (Step S5).

Next, the controller 21 determines at least one failed-image determination process to be performed on the received radiograph on the basis of the imaging part and the imaging direction indicated by the examination order information for the radiograph and/or the radiograph (Step S6).

As described above, the storage 22 stores, for each combination of the imaging part and the imaging direction, the information indicating the type(s) of a failed-image determination process(es) (e.g., name(s) of algorithm(s) therefor) to be performed on radiographs of the combination, associated with the combination, and the controller 21 determines at least one failed-image determination process to be performed on the received radiograph on the basis of the imaging part and the imaging direction, but different types of failed-image determination processes may be prepared for the same imaging part and the same imaging direction if the imaging part is a part in which metal could be embedded. In such a case, the controller 21 analyzes the received radiograph and determines whether metal is present therein, and determines on the basis of the determination result which type of failed-image determination processes is to be performed on the radiograph, the one for the case of presence of metal or the one for the case of absence of metal. Any well-known methods can be used for determining whether metal is present in radiographs. For example, there may be used a method of recognizing a metal region in a radiograph by banalization or graph cut, which is an advanced region extraction process, and determining on the basis of the recognition result whether metal is present therein.

The (at least one) failed-image determination process to be performed on the received radiograph may be determined at the time when the imaging selection button 241a is pressed, and the imaging part, the imaging direction and so forth are set. Instead of the controller 21 automatically determining the failed-image determination process to be performed, the user may select it by operating the operation unit 25. In this case, it is necessary to prevent the user from making a mistake in the selection. Hence, it is preferable that the controller 21 perform control to automatically change options of failed-image determination processes on the basis of the imaging part and the imaging direction. For example, when the imaging part is a knee, the controller 21 performs control such that a failed-image determination process about the side of a foot cannot be selected as the failed-image determination process about positioning. As another example, even when radiographs are all radiographs of the same-side ankle joint, for a radiograph obtained by imaging with a condition not supported by any failed-image determination processes prepared in the console 2, such as a radiograph obtained by weight-bearing imaging, the controller 21 performs control such that no failed-image determination process can be selected. Alternatively, types of failed-image determination processes not for the imaging part and the imaging direction indicated by examination order information for a radiograph received may be displayed distinguishably from the rest. These can prevent the user from making a mistake in the selection.

Next, the controller 21 performs the determined (at least one) failed-image determination process (Step S7). In other words, the controller 21 reads a learned model(s) M for the failed-image determination process determined in Step S6 and performs the failed-image determination process.

More specifically, in Step S7, the controller 21 first inputs the image data of the received radiograph to, among the learned models M stored in the storage 22, a learned model M for the determined failed-image determination process to cause the learned model M to infer and output an analysis result suitable for the imaging part.

The learned models M of this embodiment output numerical values as analysis results, such as "probability of the subject S imaged (radiographed) from the right (or left): X %" and "misalignment between the lateral condyle and the medial condyle: Y mm". Also, the learned models M perform, in inferring, segmentation to extract, from input radiographs, regions that are used for obtaining analysis results (e.g., regions that are used for measuring numerical values as analysis results exemplified by a region of a portion where the lateral condyle and the medial condyle are misaligned), and output images of the extracted regions.

Next, the controller 21 generates the determination result of the failed-image determination process and the determination basis information on the basis of the analysis result output by the learned model M. Examples of the determination basis information include information indicating the type of each failed-image determination process performed on a radiograph to generate the determination result, a numerical value obtained by analyzing the radiograph in the failed-image determination process and used to generate the determination result in the failed-image determination process, and a marker laid (superposed) and displayed on a region in the radiograph used to generate the determination result in the failed-image determination process.

For example, when generating the determination result of the failed-image determination process about the wrong-side part, the controller 21 compares the probability of the subject S imaged from the right with the probability of the subject S imaged from the left, and determines that the subject S is imaged from a direction having a higher probability.

If the determined direction is different from the imaging direction supposed to be of the received radiograph (imaging direction indicated by examination order information), the controller 21 generates textual information "Right-or-Left Check" as the determination result of the failed-image determination process. The controller 21 generates, as the determination basis information, textual information indicating the type of (e.g., name of the algorithm for) the failed-image determination process performed and textual information indicating the probability of the subject S imaged from the right and/or the probability of the subject S imaged from the left. Alternatively, the controller 21 may generate and use the textual information "Right-or-Left Check" as it is, as the determination basis information.

As another example, when generating the determination result of the failed-image determination process about the misalignment between the lateral condyle and the medial condyle, which is a specific example of positioning, the controller 21 generates, on the basis of the analysis result (misalignment amount) output by the learned model M in the form of a numerical value, the determination result of the failed-image determination process in the form of a rank corresponding to a level of the possibility that imaging has failed (imaging failure).

More specifically, the controller 21 refers to preset determination criteria (reference values) and assigns one of ranks to the generated analysis result (misalignment amount between the lateral condyle and the medial condyle).

For example, the controller 21 assigns "Rank A (Good)" when the generated analysis result is less than a first reference value (the possibility of imaging failure is low (or lowest)), assigns "Rank B (Acceptable)" when the generated analysis result is equal to or greater than the first reference value but less than a second reference value, and assigns "Rank C (Re-imaging)" when the generated analysis result is equal to or greater than the second reference value (the possibility of imaging failure is high (or highest)), and generates textual information indicating the rank, which is assigned to the misalignment amount as the analysis result, as the determination result of the failed-image determination process.

The number of ranks may be two, such as "Rank A/B" and "Rank C" with one reference value, or may be four or more with three or more reference values.

The controller 21 generates, as the determination basis information, textual information indicating the type of (e.g., name of the algorithm for) the failed-image determination process performed and textual information indicating the misalignment amount. The controller 21 also generates, as the determination basis information, a colored marker superposed on the portion where the lateral condyle and the medial condyle are misaligned, on the basis of the radiograph from which the portion has been extracted.

When finishing the (at least one) failed-image determination process, the controller 21 causes the display 24 to display the determination result(s) of the failed-image determination process(es) and the determination basis/bases (Step S8).

Figure 4:
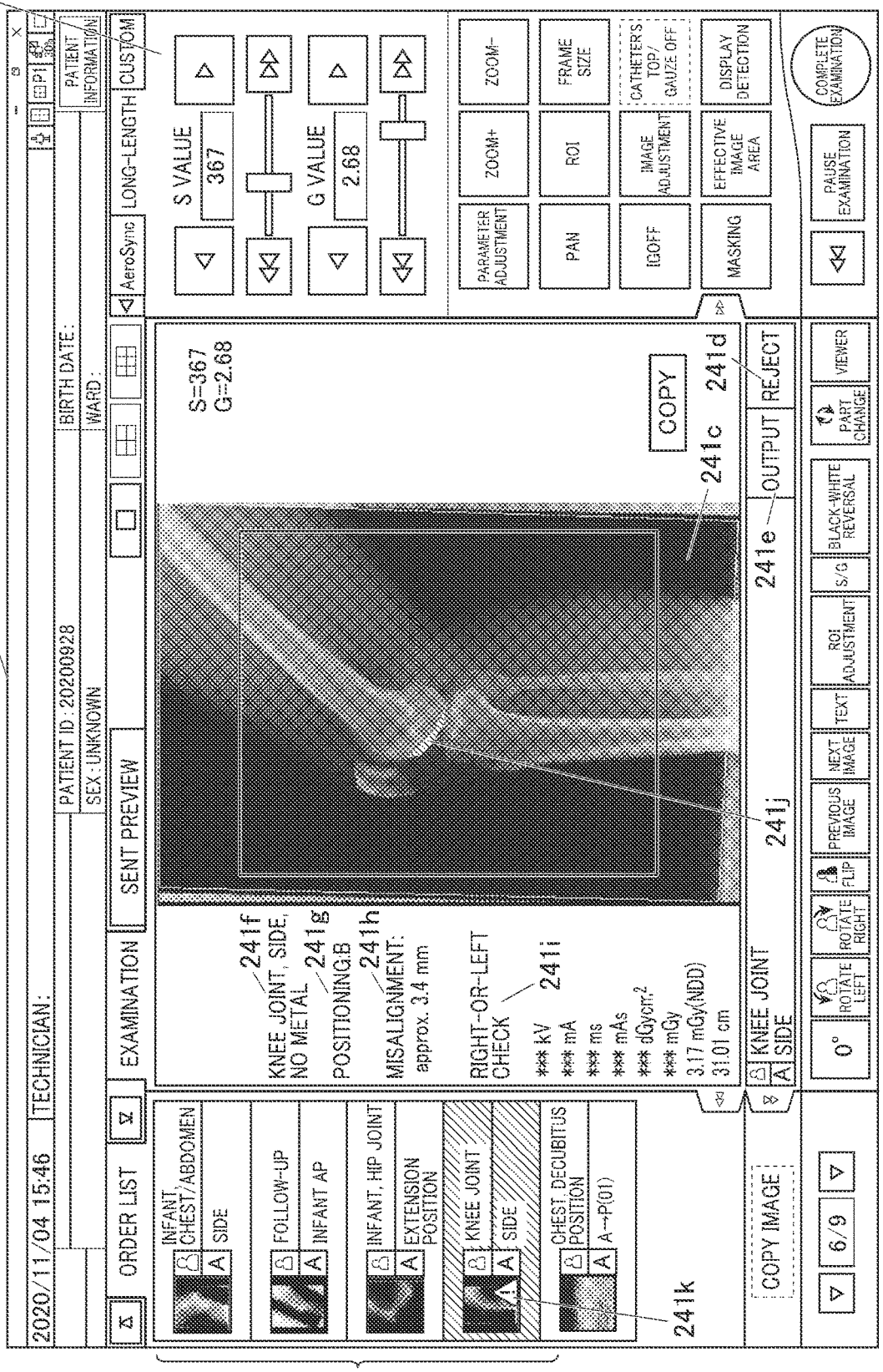
FIG. 4 shows a display example of determination results of failed-image determination processes and determination bases (determination basis information)

FIG. 4 shows an example of the examination screen 241 where a preview image of a radiograph obtained from the imaging apparatus 1, determination results of two failed-image determination processes performed and determination basis information are displayed.

As shown in FIG. 4, in Step S8, in the image display area 241c of the examination screen 241, a preview of the received radiograph is displayed. Also, the determination results (241g, 241i in FIG. 4) of the failed-image determination processes performed on the radiograph, which is displayed, and the determination basis information (241f, 241h, 241i, 241j in FIG. 4) are displayed. Also, an alert 241k is displayed. The alert 241k represents presence of a determination result(s) indicating imaging failure.

The "Knee Joint, Side, No Metal" denoted by 241f is the name of the algorithm for the failed-image determination process about positioning performed on the received radiograph and is information indicating the type of the failed-image determination process performed. The "Positioning: B" denoted by 241g is the determination result of this performed failed-image determination process. The "Misalignment: approx. 3.4 mm" denoted by 241h is the misalignment amount between the lateral condyle and the medial condyle and is the numerical value obtained by analyzing the radiograph and used as the determination basis information to generate the determination result denoted by 241g. The "Right-or-Left Check" denoted by 241i indicates the name of the algorithm for the failed-image determination process about wrong-side part performed on the received radiograph and also indicates the determination result of the failed-image determination process performed. The name of the algorithm for the failed-image determination process about wrong-side part may be more specific by addition of the imaging pan, such as "Knee Joint, Side, Right or Left", like the name of the algorithm for the failed-image determination process about positioning. The indicator denoted by 241j (region indicator 241j) is a colored marker attached to and superposed on the region of the portion where the lateral condyle and the medial condyle of the knee joint (femur) are misaligned in the radiograph, and is the determination basis information based on which the rank about positioning has been determined as B.

Conventionally, the determination result as to whether an image is a failed image and the image itself, about which the determination result has been made, are displayed, but neither what kind of failed-image determination process has been used nor for what reason the image has been determined as a failed image, namely, the basis for the determination (determination basis information), is displayed. This has caused a problem that the user can hardly accept the determination result. In this embodiment, however, the console 2 outputs the basis/bases for each determination result. This allows the user to check whether appropriate failed-image determination processes have been performed on a radiograph and can improve user's satisfaction with the determination results, and consequently can assist the user in making a quick decision as to whether the radiograph is a failed image and whether re-imaging is necessary.

Further, the determination results are displayed at the stage of preview display before imaging finishes. This allows the user to decide whether re-imaging is necessary before imaging finishes.

The user checks a radiograph, a determination result(s) of a failed-image determination process(es) performed on the radiograph, the basis/base for the determination results(s) and so forth, makes the final decision as to whether the radiograph is a failed image, and presses the reject button 241d if he/she decides that the radiograph is a failed image (re-imaging is necessary).

An indicator of a region (region indicator 241j in FIG. 4) in a radiograph used to determine whether the radiograph is a failed image and displayed on the radiograph as the basis for the determination is annoying if it is always displayed. Further, the indicator is merely a reference. Hence, it is preferable that the region indicator 241j do not become an obstacle for the user to check the radiograph.

It is therefore preferable that a switch that toggles the region indicator 241j between ON (display) and OFF (hide) be provided.

Figure 5:
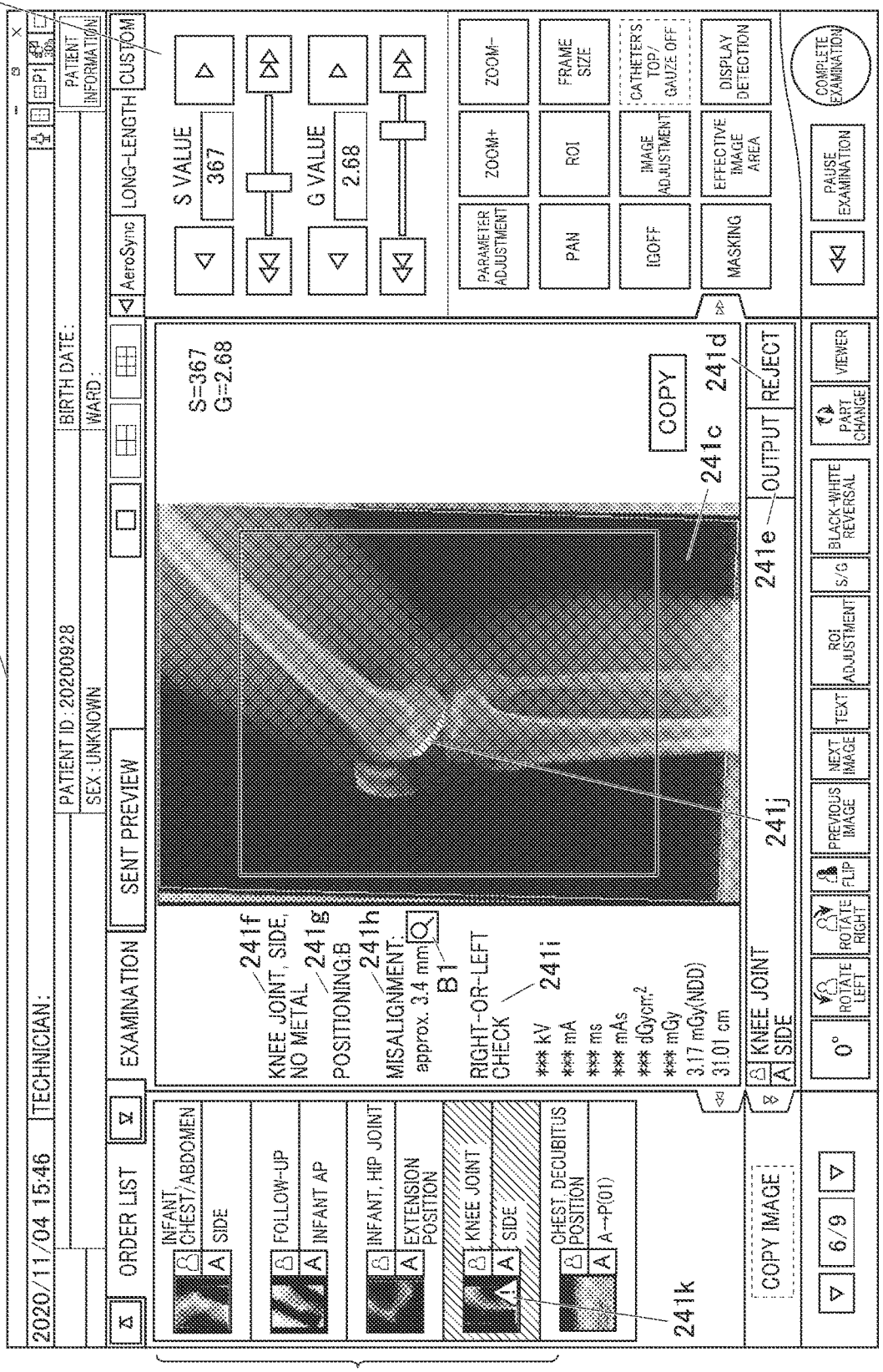
FIG. 5 shows an example of a switching button that toggles a marker as a region indicator shown in FIG. 4 between ON and OFF.

For example, as shown in FIG. 5, an ON/OFF button B1 for the region indicator 241j may be provided in the vicinity of the determination result (241g) and the determination bases (241f, 241h) relevant to the region indicator 241j, and the controller 21 may turn on or off the region indicator 241j in response to a press on the button B1 with the operation unit 25.

Figure 6:
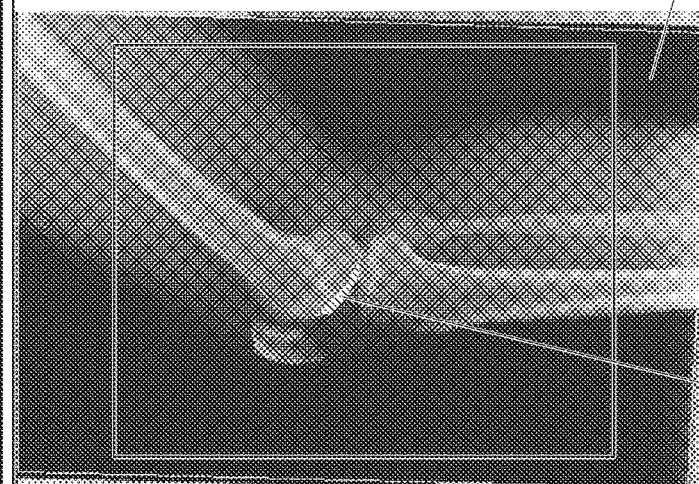
FIG. 6 shows an example of the switching button that toggles the marker as the region indicator shown in FIG. 4 between ON and OFF.

Alternatively, as shown in FIG. 6, the displayed determination result (241g) and determination bases (241f, 241h) relevant to the region indicator 241j themselves may each be an ON/OFF button for the region indicator 241j, and the controller 21 may turn on or off the region indicator 241j in response to a press on any of the determination result (241g) and the determination bases (241f, 241h).

Figure 7:
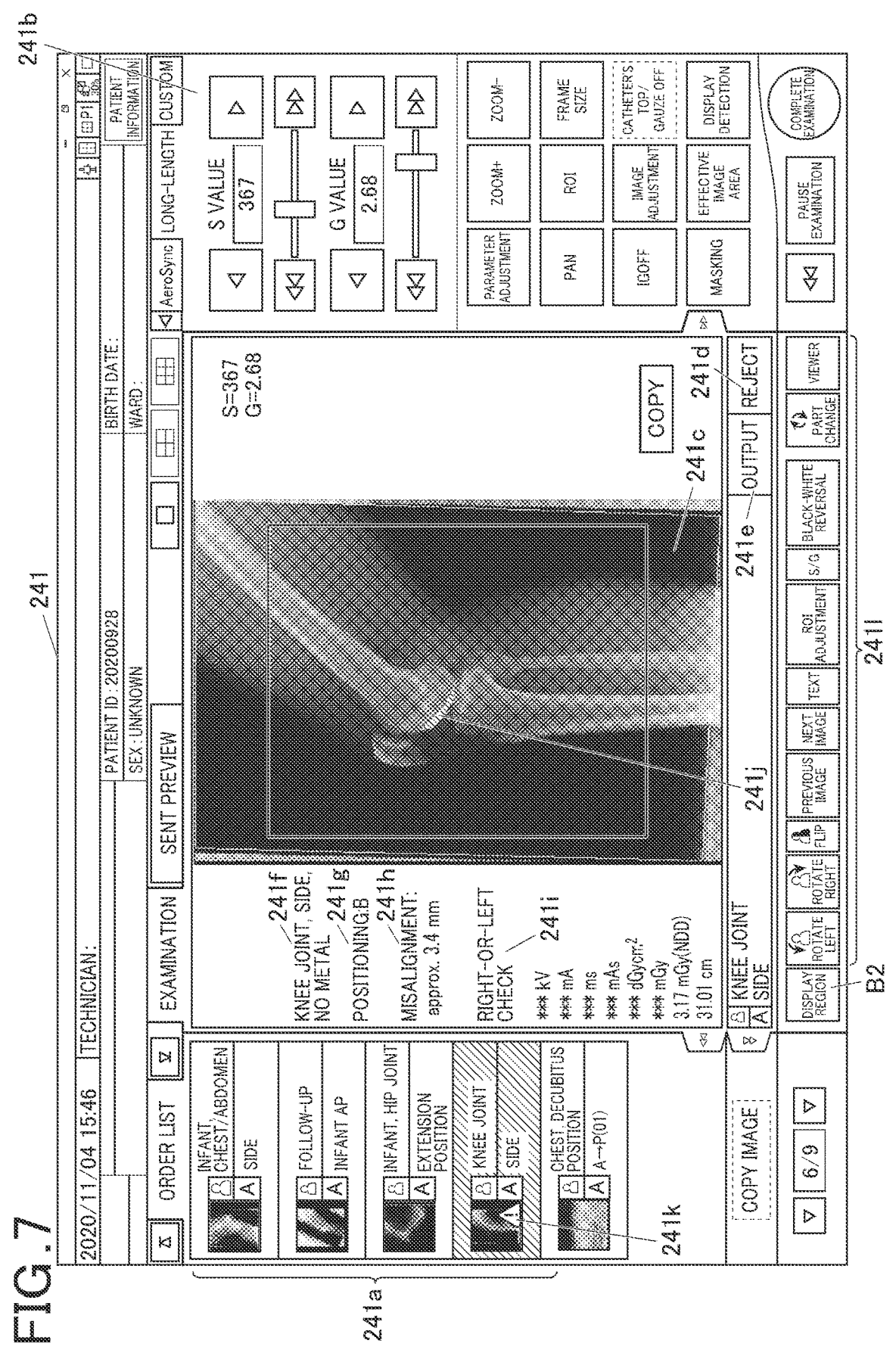

Still alternatively, as shown in FIG. 7, on the same row as simple buttons 4211, which include buttons for rotating images, an ON/OFF button ("Display Region") B2 for the region indicator 241j may be provided, and the controller 21 may turn on or off the region indicator 241j in response to a press on the button B2 with the operation unit 25.

Figure 8:
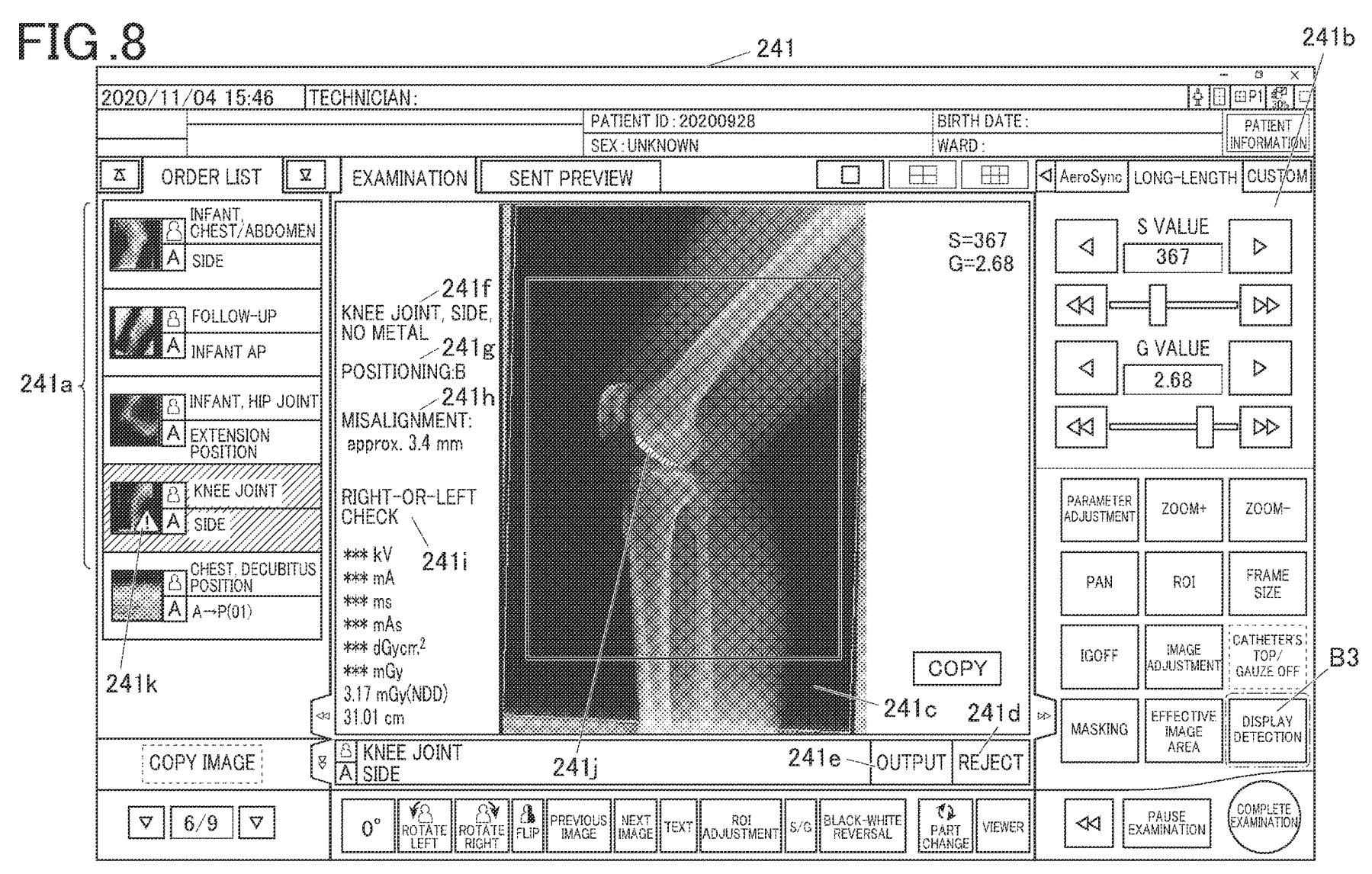

Yet alternatively, as shown in FIG. 8, as one of buttons for advanced adjustment of image processing conditions, which include buttons for adjustment of image density and adjustment of frequency, displayed in the setting area 241b, an ON/OFF button ("Display Detection") B3 for the region indicator 241j may be provided, and the controller 21 may turn on or off the region indicator 241j in response to a press on the button B3 with the operation unit 25.

Figure 9:
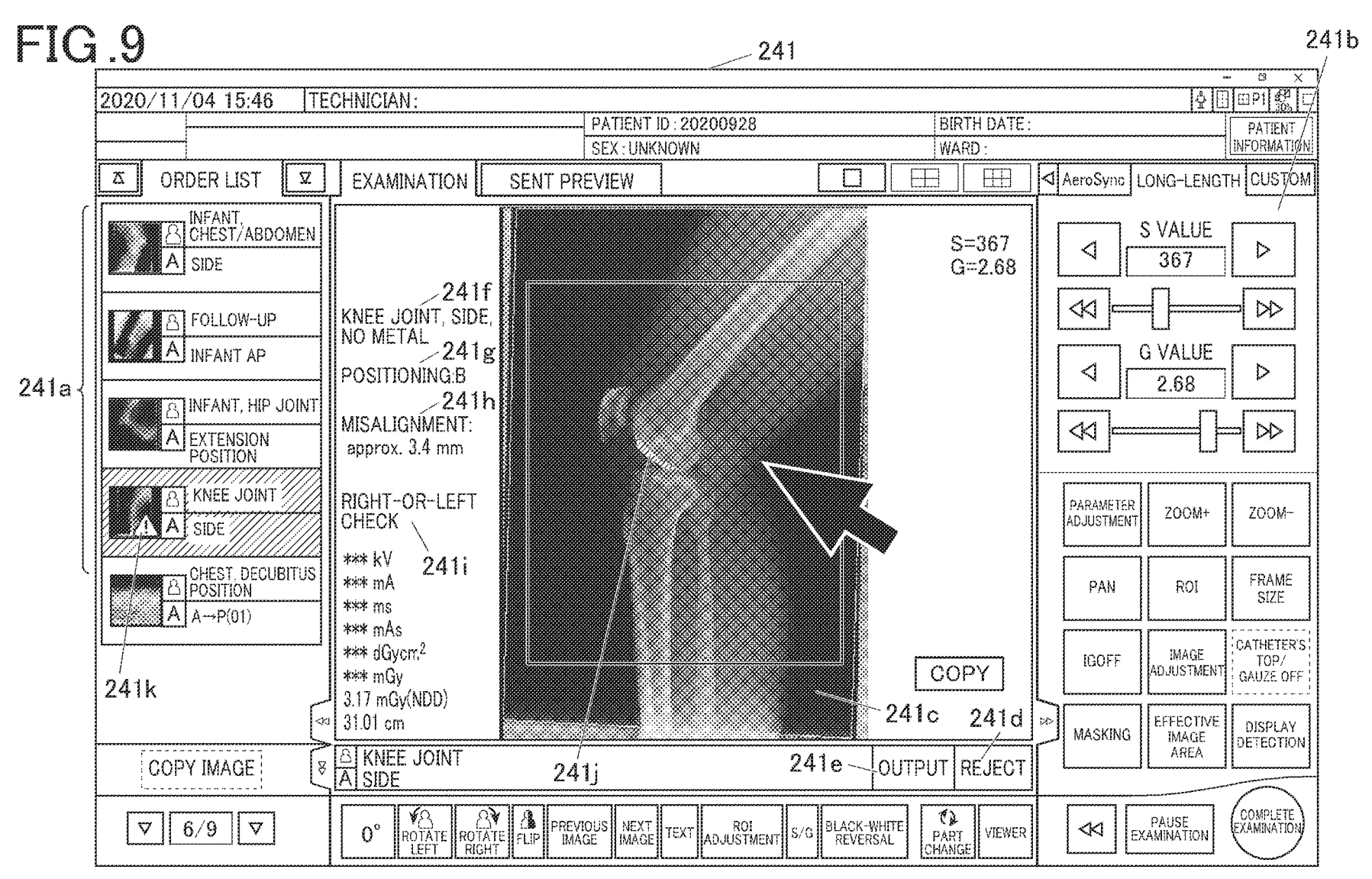

Alternatively, as shown in FIG. 9, the radiograph displayed in the image display area 241c may be used as an ON/OFF button for the region indicator 241j, and the controller 21 may turn on or off the region indicator 241j in response to a press on the radiograph with the operation unit 25.

The determination criteria for determining the rank about positioning are different from imaging part to imaging part, from facility to facility, from imaging conditions to imaging conditions, and so forth. If the region indicator 241j is always displayed in the same color, it is hard for the user to know the rank. Hence, it is preferable that the controller 21 change the color of the region indicator 241j in accordance with the determination result (rank) (e.g., blue for Rank A, yellow for Rank B, and red for Rank C).

Figure 10:
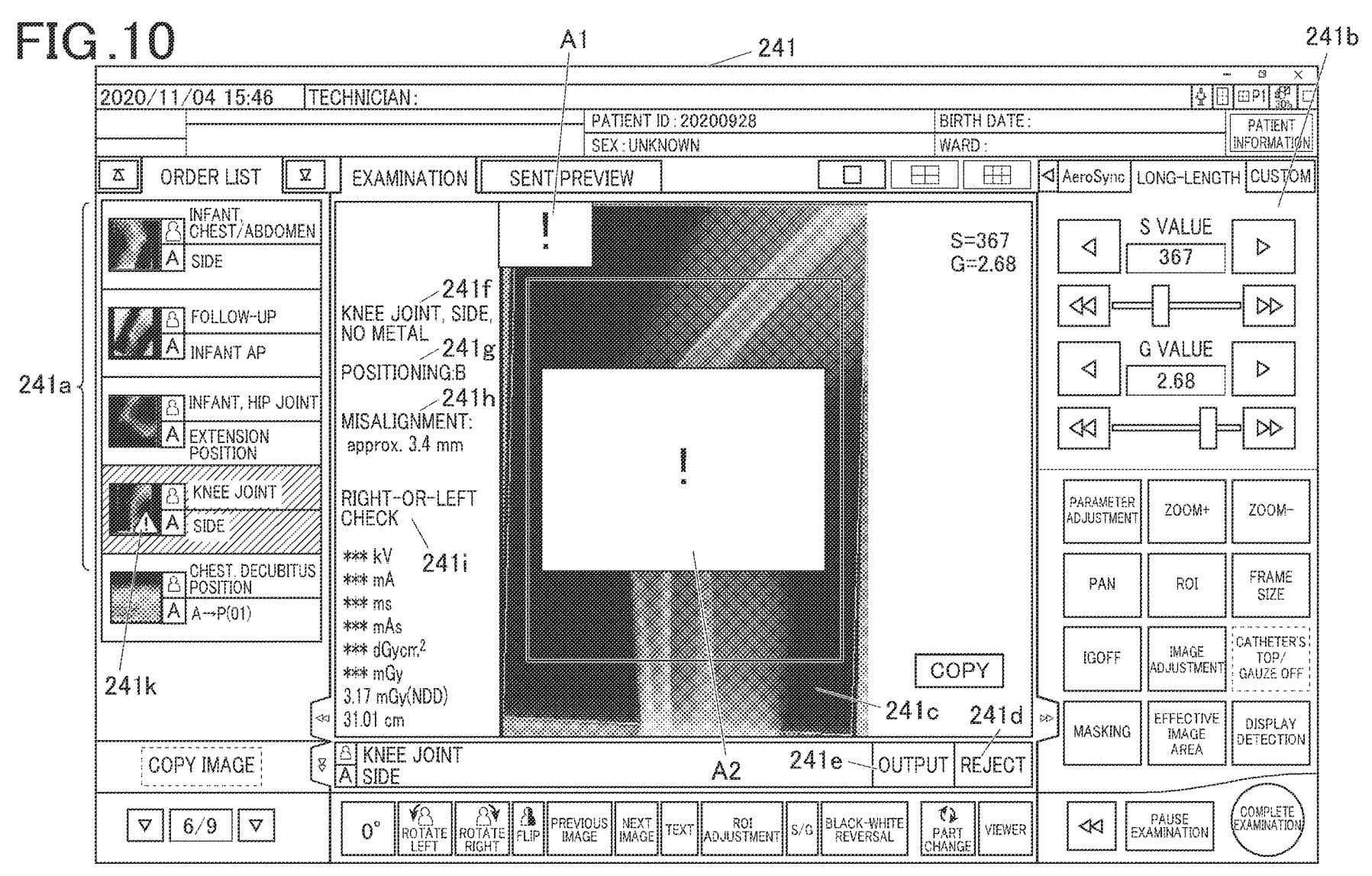

Further, if the determination result is not good, the possibility of re-imaging is high, and hence it is necessary for the user to be aware of the result immediately. It is therefore preferable that the controller 21 cause the display 24 to display an alert in a different mode in accordance with the rank of the determination result. For example, as shown in FIG. 10, when the rank of the determination result is B, an alert A1 of a predetermined size not to cover the subject (imaging part) is displayed, whereas when the rank of the determination result is B, an alert A2 of a larger size to cover the subject (imaging part) is displayed. Alternatively, when the rank of the determination result is B, an alert (e.g., 241k in FIG. 4) may be displayed on a thumbnail image on its corresponding imaging selection button 241a, whereas when the rank of the determination result is C, the alert may be displayed on the text side of the imaging selection button 241a to be more noticeable, or may be displayed, as shown in FIG. 10, on the radiograph.

Further, there are some cases where the determination result is incorrect. Examples of the cases include a case where the determination result is incorrect due to wrong selection of (the algorithm for) a failed-image determination process. Then, it is necessary, for example, to re-perform the failed-image determination process (re-processing). Hence, it is preferable that, in Step S8, the controller 21 cause the display 24 to display a not-shown re-processing button or the like on the examination screen 241, and perform the failed-image determination process again in response to a press on the re-processing button. At the time, the controller 21 may select and perform a failed-image determination process different from the already-used failed-image determination process, automatically or in response to an operation made by the user.

Further, if a failed-image determination process performed on a radiograph obtained by imaging with the imaging part, the imaging direction, the modality and/or the like not supported by any failed-image determination processes prepared in the console 2, and the determination result is somehow generated, the determination result, which is wrong, is displayed. This is undesirable. Hence, if a radiograph received is an image not supported by any prepared failed-image determination processes, it is preferable that the controller 21 do not perform any failed-image determination processes and cause the display 24 to display a message indicating that the radiograph is an image not supported, such as "Unanalyzable", on the examination screen 241.

Further, if the region indicator 241j is always displayed, it becomes an obstacle for the user to make operations for image processing (e.g., an operation to adjust image density, an operation to adjust frequency, an operation to zoom, etc.) for the radiograph displayed in the image display area 241c. Hence, when the user starts making a predetermined operation (e.g., an operation to adjust image density, an operation to adjust frequency, an operation to zoom, etc.) while the region indicator 241j is displayed, it is preferable that the controller 21 perform control to automatically hide the region indicator 241j.

When the user finishes the predetermined operation, the controller 21 may automatically turn on (display) the region indicator 241j, or leave it as it is (OFF/hidden).

Figure 11:
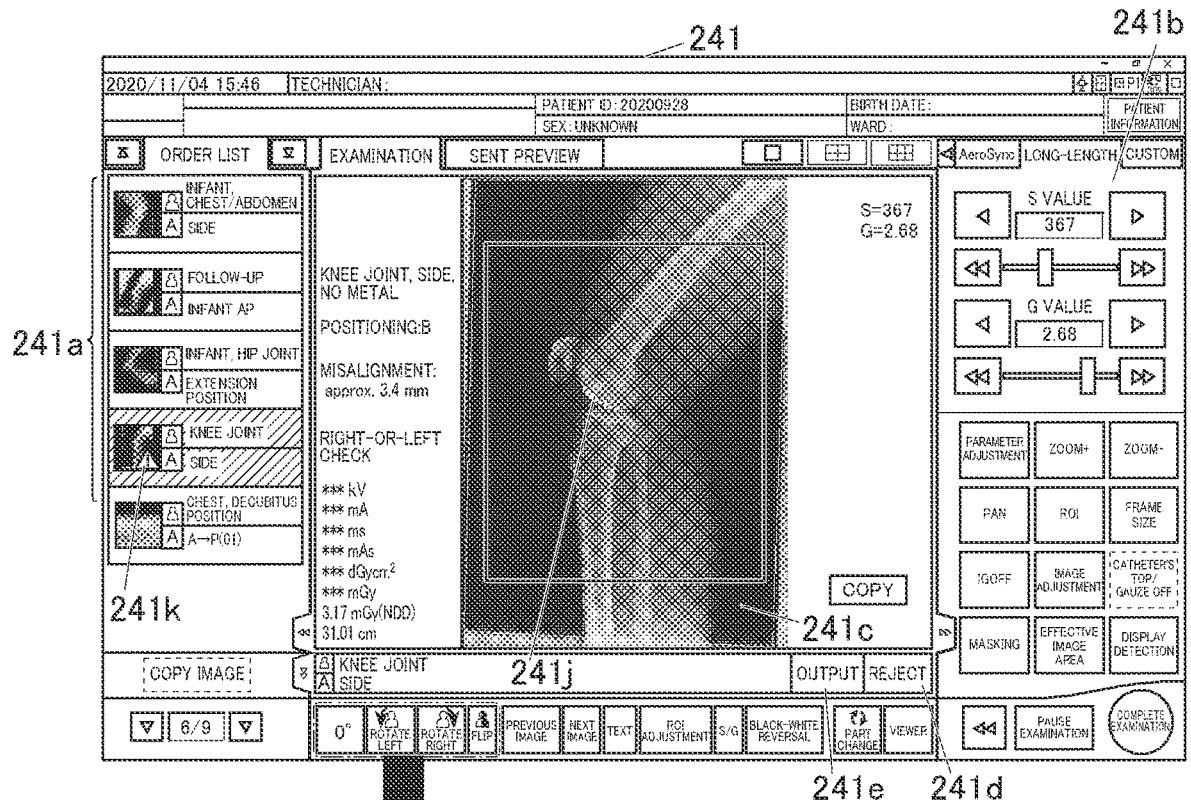
FIG. 11 shows a state in which the region indicator shown in FIG. 4 is rotated in response to a rotation operation made for a radiograph displayed.
Figure 11:
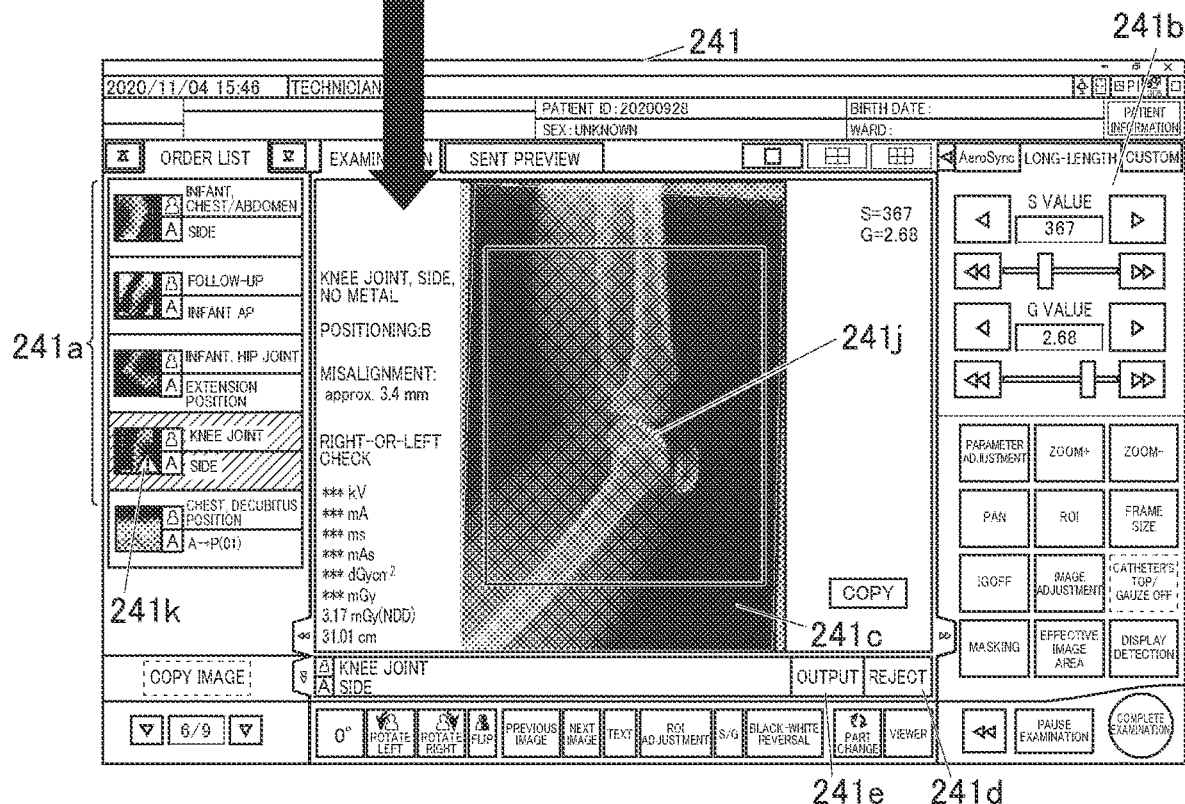

Further, when the user makes an operation to change the shape, size or position of the radiograph displayed, such as an operation to rotate, flip, enlarge, reduce, pan or move the radiograph, he/she may want to see the region indicator 241j after the change too. Hence, when the user makes an operation to change the shape, size or position of the radiograph displayed in the image display area 241c with the operation unit 25, the controller 21 performs control such that the region indicator 241j is displayed following the change in the radiograph. For example, as shown in FIG. 11, when the radiograph is rotated, the region indicator 241j is rotated by the same angle as that by which the radiograph is rotated. The region indicator 241j may be hidden while the radiograph is being changed in shape or the like, and may be displayed after the radiograph is changed in shape or the like to follow the change in the radiograph. This can reduce processing load. In the case where the processing load is small even if the region indicator 241j is displayed while the radiograph is being changed in shape or the like, for example, being panned, following the change in the radiograph, the region indicator 241j may be displayed while the radiograph is being changed in shape or the like too following the change in the radiograph.

Further, the region indicator 241j overlaps with the subject region. Hence, when a foreign matter or an abnormal growth is present thereunder, it is hard to see. It is therefore preferable that the controller 21 perform control to display the region indicator 241j having a transparency of a predetermined threshold value or greater (e.g., 30% or greater).

Further, depending on the background density, the region indicator 241j may be hard to see. For example, the region indicator 241j is harder to see in a high signal area (black) than in a low signal area (white). Hence, it is preferable that the controller 21 change the color and/or the transparency of the region indicator 241j according to the background density of the region indicator 241j. For example, when the signal value of the background of the region indicator 241j is of a high signal area (the signal value is higher than a predetermined threshold value), the controller 21 performs control to automatically reduce the transparency of the region indicator 241j, border the region indicator 241j, or increase the density of the region indicator 241j.

In the case where the region indicator 241j is bordered (with a frame line), if the border thickness is always the same, depending on the border thickness, the region indicator 241 may be hard to see by being crushed when the radiograph is reduced. Hence, it is preferable that the controller 21 automatically adjust the border thickness according to the scale of reduction/enlargement.

Further, easy-to-see density and color are different from person to person. Hence, it is preferable that the density and color of the region indicator 241j can be changed. There may be therefore provided a setting unit for the user to set and change the density, border thickness and color of the region indicator 241j, and the controller 21 may perform control to display the region indicator 241j with the set density, border thickness and color. Further, it is hard for the user to distinguish region indicators when they are in the same color. Hence, when the color can be changed by the user, it is preferable that the controller 21 perform control such that the color of a region indicator, which is an already selected color, and its similar colors are not displayed as options for the color of another region indicator, and accordingly not selectable.

Figure 12:
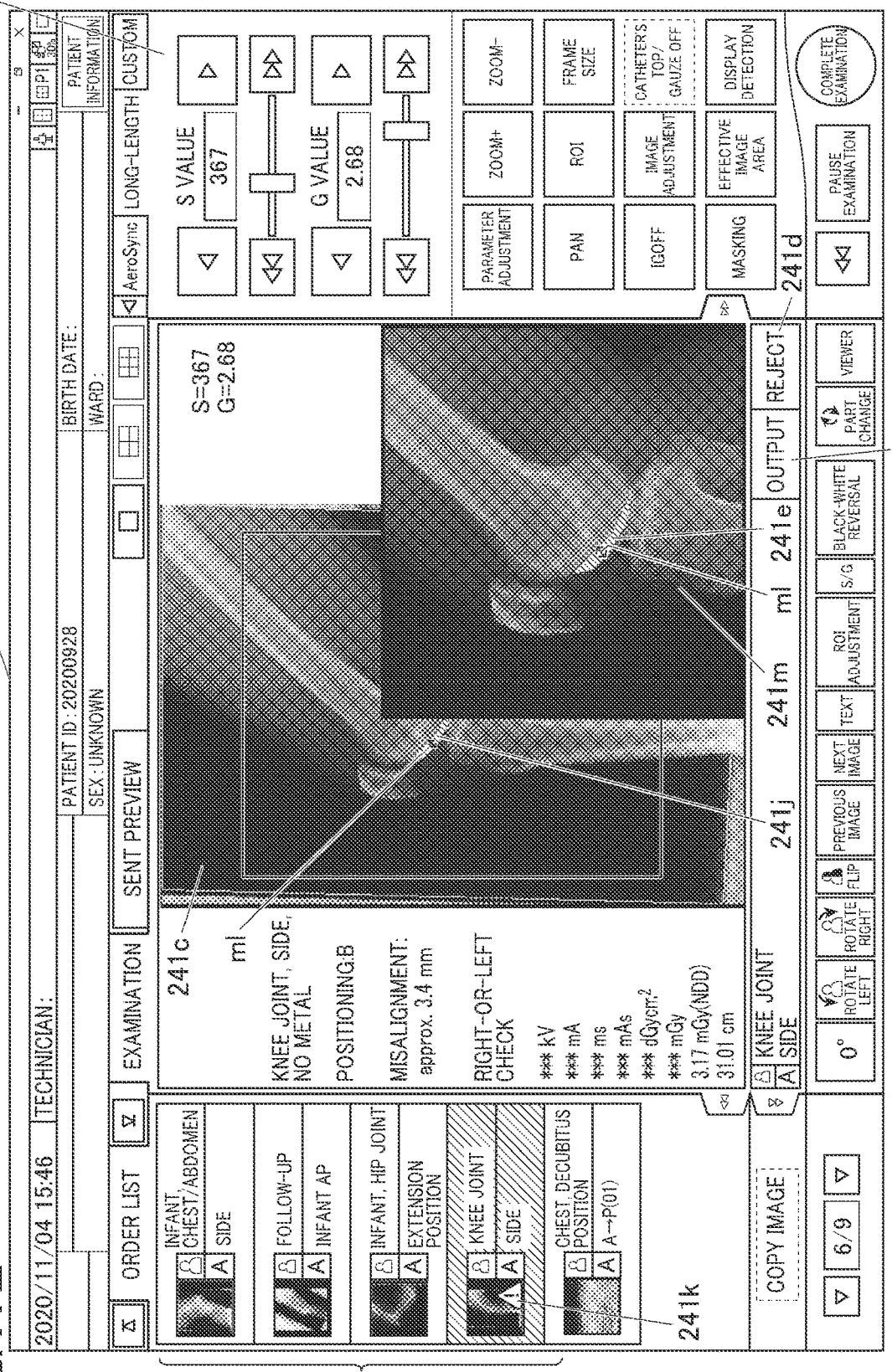
FIG. 12 shows a state in which the region indicator is enlarged and displayed when it is small.

Further, not knowing where has been measured to obtain the misalignment amount used to generate the determination result about positioning makes user's satisfaction with the determination result low. Hence, as shown in FIG. 12, it is preferable that the controller 21 perform control to display the measurement position of the misalignment amount on the radiograph with a marker ml exemplified by a double-headed arrow.

Further, the region indicator 241j that is small is hard to see, and also makes it hard to see the marker ml thereon. Hence, when the region indicator 241j is small (e.g., when the area of the region indicator 241j is equal to or less than a predetermined threshold value), the controller 21 may perform control to display the region indicator 241j and/or the marker ml on an enlarged image 241m that focuses on the region portion where the region indicator 241j is displayed. The enlarged image 241m may be a pop-up, for example.

Returning to FIG. 3, the controller 21 determines whether the reject button 241d has been pressed with the operation unit 25 (Step S9).

If the controller 21 determines that the reject button 241d has been pressed with the operation unit 25 (Step S9; YES), the controller 21 associates and saves in the storage 22 the radiograph decided as a failed image with a flag indicating that the radiograph is a failed image, the determination result(s) of the failed-image determination process(es) performed, the determination basis/bases, the part information, the technician-in-charge information and so forth (Step S10). Associating and saving/accumulating in the storage 22 the radiograph with the flag indicating that the radiograph is a failed image, the determination result(s) of the failed-image determination process(es) performed, the determination basis/bases, the part information, the technician-in-charge information and so forth is useful for educating/training radiographers.

After pressing the reject button 241d, the user resets imaging conditions and/or redoes positioning, and then performs re-imaging.

Then, the controller 21 returns to Step S4 (or Step S3) to repeat Step S4 (or Step S3) to Step S8.

Figure 13:
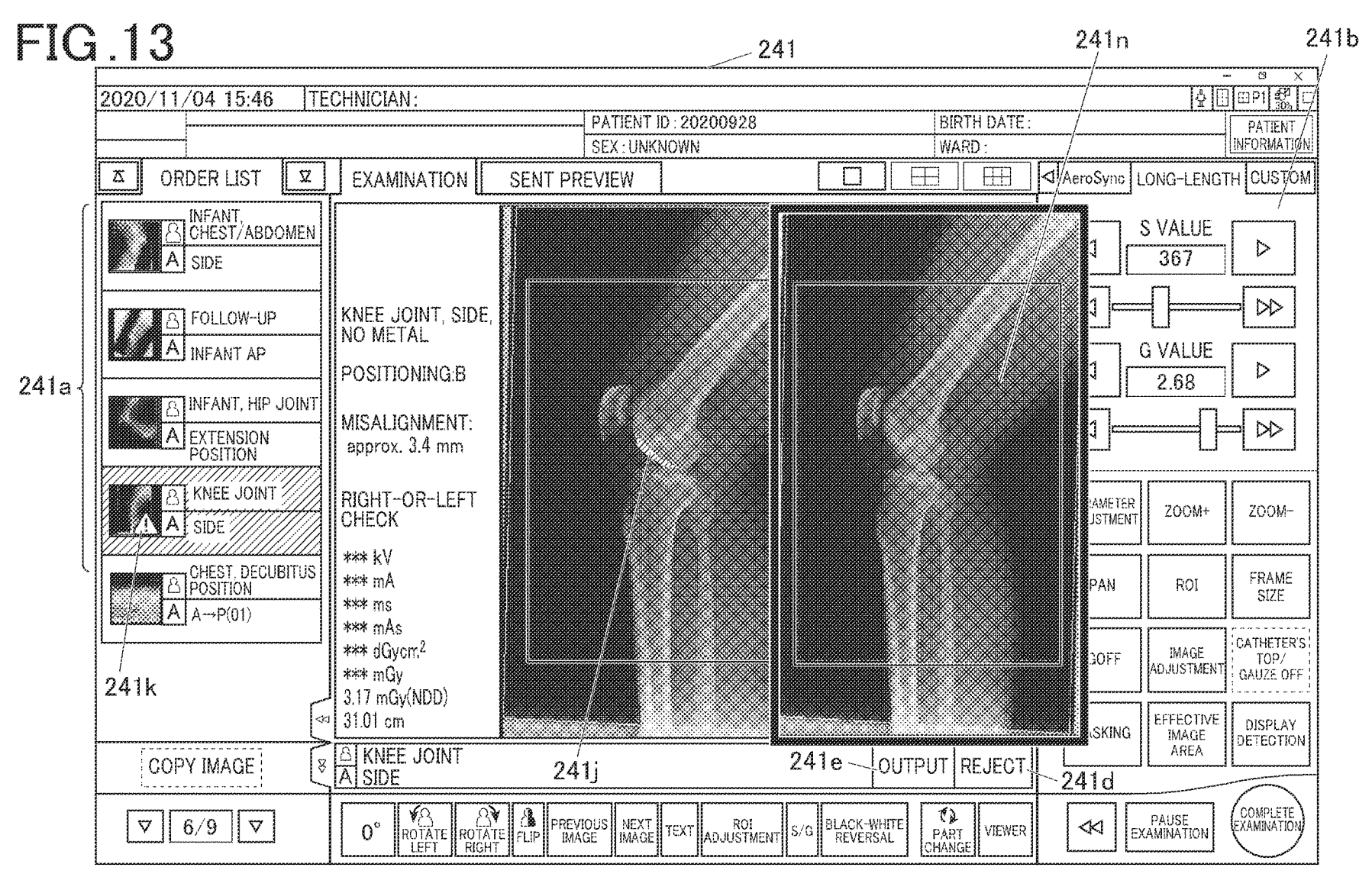

If there is no image serving as a target image for re-imaging, the user may not know how to change positioning or imaging conditions. Hence, the controller 21 may generate, by using GAN (Generative Adversarial Networks, one of machine learning methods) or the like, a properly-taken target image 241n shown in FIG. 13 as a reference for re-imaging, and present the target image 241n on the examination screen 241. For example, by using machine learning, such as GAN, a learned model has been generated by being trained with data patterns of images obtained with error in positioning (misalignment) and images having a misalignment amount of 0 (zero) obtained with the error in positioning corrected, and the controller 21 generates the properly-taken target image 241n by inputting the radiograph decided as a failed image to the learned model, and causes the target image 241n to be displayed alongside the radiograph. This allows the user to perform re-imaging, referring to a target image.

In Step S9, if the controller 21 determines that the reject button 241d has not been pressed with the operation unit 25 (Step S9; NO), the controller 21 performs predetermined image processing on the radiograph, and causes the display 24 to display, as the final image, the processed radiograph in the image display area 241c (Step S11).

If the user operates an image processing condition or the like in the setting area 241b, the controller 21 performs image processing on the radiograph in accordance with the operation made by the user.

The controller 21 determines whether the output button 241e has been pressed with the operation unit 25 (Step S12). If the controller 21 determines that the output button 241e has not been pressed (Step S12; NO), the controller 21 returns to Step S9.

If the controller 21 determines that the output button 241e has been pressed (Step S12; YES), the controller 21 associates and saves in the storage 22 the radiograph generated as the final image with a flag indicating that the radiograph is not a failed image, the determination result(s) of the failed-image determination process(es) performed, the determination basis/bases, the part information, the technician-in-charge information and so forth, and also associates and sends to the image management apparatus 4 via the communication unit 23 the radiograph generated as the final image with patient information and examination information (examination ID, examination date, imaging part, imaging direction, etc.) (Step S13), and then ends the imaging control process.

As described above, the controller 21 of the console 2 performs, among multiple types of failed-image determination processes, at least one failed-image determination process on a radiograph received from the imaging apparatus 1, thereby generating a determination result(s) and determination basis information indicating the basis/bases for the determination result(s). Then, the controller 21 causes the display 24 to output the determination result and the determination basis information.

This allows the user to check whether appropriate failed-image determination processes have been performed on a radiograph and can improve user's satisfaction with the determination results, and consequently can assist the user in making a quick decision as to whether the radiograph is a failed image and whether re-imaging is necessary.

It is needless to say that the present invention is not limited to the above embodiment(s) or the like but can be appropriately modified within a range not departing from the scope of the present invention.

For example, in the above embodiment, failed-image determination processes are performed by analyzing a radiograph by machine learning, but may be performed by analyzing a radiograph by image processing.

Further, in the above embodiment, the function of the failed-image decision support apparatus is installed in the console 2, but may be installed in an apparatus different from the console 2 or in a dedicated apparatus.

Further, in the above embodiment, the controller 21 of the console 2 causes the display 24 as an outputter to display the determination results of failed-image determination processes and the determination basis information, but may cause a display apparatus separate from the console 2 to display these. In other words, the controller (hardware processor) and the outputter of the present disclosure may be installed in different apparatuses and constitute a failed-image decision support system.

Further, the determination results of failed-image determination processes and the determination basis information may be output as audio by a not-shown audio output apparatus, in addition to or instead of being displayed.

Further, the controller 21 of the console 2 may perform control to output (send/transmit) the generated determination results and determination basis information to an external apparatus (external system) in addition to or instead of the outputter (display 24). Examples of the external apparatus includes the image management apparatus 4 (PACS), a dose management apparatus, an RIS and a personal digital assistant (PDA) for business use.

For example, the controller 21 causes the communication unit 23 to output, to an external apparatus, textual information and/or numerical value information (e.g., length of the misalignment, coordinate information of the region of the portion where the misalignment occurs, etc.) of the determination results and the determination basis information.

Figure 14A:
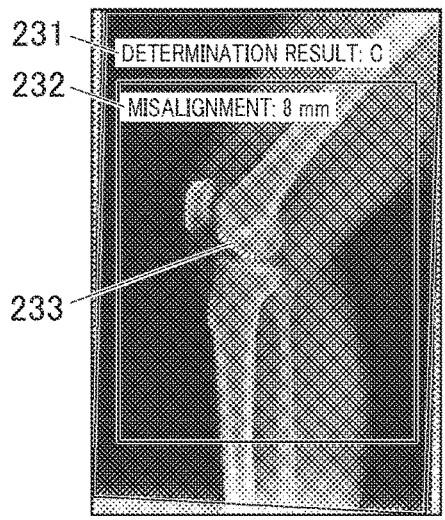
FIG. 14A shows an example of image information of determination basis information to be output.
Figure 14B:
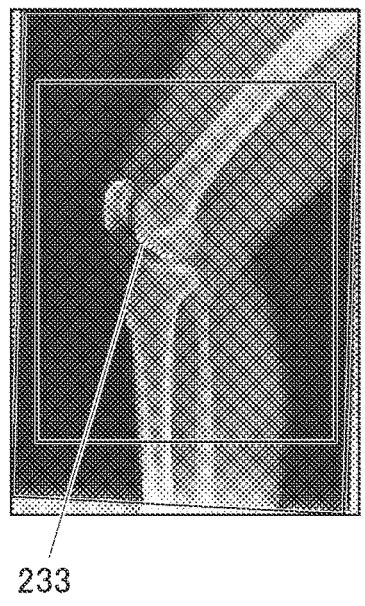
FIG. 14B shows an example of the image information of the determination basis information to be output.
Figure 14C:
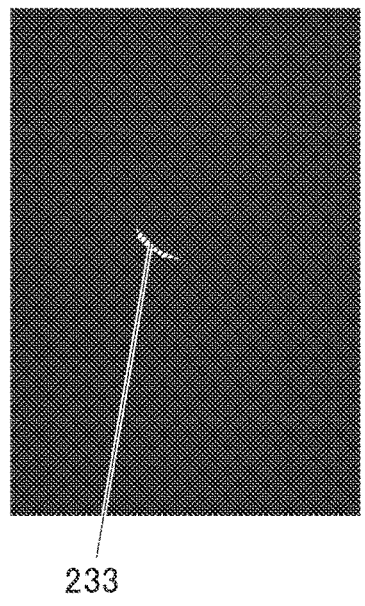
FIG. 14C shows an example of the image information of the determination basis information to be output.

Alternatively or additionally, the controller 21 may cause the communication unit 23 to output, to an external apparatus, image information of the determination results and the determination basis information. For example, the controller 21 may generate, as shown in FIG. 14A, an image in which a determination result 231 and determination basis information 232, 233 are laid on a radiograph used for the determination, and cause the communication unit 23 to output the image to an external apparatus. Alternatively, the controller 21 may generate, as shown in FIG. 14B, an image in which the determination basis information (information indicating a region that is a determination basis) 233 is laid on the radiograph used for the determination, and cause the communication unit 23 to output, to an external apparatus, the image together with textual information of the determination result (e.g., "Determination Result: C") and textual information of the other determination basis information (e.g., "Misalignment: 8 mm"). Still alternatively, the controller 21 may generate, as shown in FIG. 14C, a background-removed image of the determination basis information 233, and cause the communication unit 23 to output, to an external apparatus, the image together with the textual information of the determination result (e.g., "Determination Result: C"), the textual information of the other determination basis information (e.g., "Misalignment: 8 mm") and the radiograph used for the determination. Examples of the file format of the image information to be output are not limited to but include JPEG, BMP, PNG, TIFF and GIF.

Further, there may be provided settings to, in accordance with the determination result of a failed-image determination process, change the destination to which the determination result and the determination basis information are output, to output or not to output these, and to change the information to be output. On the basis of these settings, the controller 21 may control, in accordance with the determination result of a failed-image determination process, output of the determination result and the determination basis information.

For example, there may be provided a setting for the controller 21 to perform control to output, to a dose management system, only the determination results of failed-image determination processes and the determination basis information about radiographs decided in the end as failed images. Further, if there is a radiograph (imaging) about which the determination result of a failed-image determination process is wrong, such as a radiograph determined as a failed image or so (e.g., Rank B or Rank C) in a failed-image determination process but not actually decided as a failed image, the controller 21 may perform control to output the determination result and the determination basis information about the radiograph to another destination, such as a customer support center, after requesting and obtaining permission to do so from the operator. Further, the controller 21 may perform control to output, as the determination basis information, the radiograph analyzed (used for the determination). Further, when a plurality of radiographs has been taken in one examination by video imaging, long-length imaging, in which radiographs are combined, or the like, the controller 21 may perform control to output, among the radiographs on which a failed-image determination process(es) has been performed, only a radiograph(s) that has served as the basis for the determination result. Further, if a radiograph has a region unneeded for the determination, such as a region where the subject S (imaging part) is not captured, the controller 21 may trim the radiograph and perform control to output only a portion of the radiograph (trimmed radiograph). Further, the controller 21 may perform control to also output the program(s) of failed-image determination processes performed on a radiograph and parameters, such as threshold values used for the determination, so that the failed-image determination processes can be re-performed at the destination.

The timing at which the determination results and the determination basis information are output to an external apparatus is not limited to but may be the timing at which the output button 241e is pressed or the timing at which a "Complete Examination" button (shown in FIG. 4, etc.) is pressed.

In the above embodiment, the determination results of failed-image determination processes and the determination basis information are displayed together with a preview image, but may be displayed together with the final image on which image processing has been performed. After completion of imaging, at the time when a radiograph from an examination list is displayed again, the determination result(s) is displayed, but the indicator(s) (e.g., marker(s)), which is displayed on the radiograph, is not displayed.

Further, in the above embodiment, the present invention is applied to determination as to whether radiographs are failed images, but may be applied to determination as to whether other medical images (e.g., RMI images, ultrasound images, etc.) are failed images.

Further, for example, in the case of follow-up imaging, at the time of imaging, the positioning (body position, etc.) and the part being the right part or the left part at the time of imaging last time cannot be checked. Hence, the radiograph taken this time may be different from the previous one in positioning and/or right/left part.

Then, in the console 2, the controller 21 may obtain the previous radiograph of the same part of the same patient from the image management apparatus 4 or the like at the time when examination order information comes in (is received), apply the learned model M that determines whether the imaging part is the right part or the left part to the previous radiograph, thereby determining whether the part captured in the previous radiograph is the right part or the left part, and output an alert by display or audio if the part captured in the previous radiograph is different from (opposite to) the part indicated by the examination order information this time. This can find, in the case of follow-up imaging based on previous radiographs, doctors' order mistakes before patients are irradiated.

Further, on rare occasions, imaging is performed with a body position different from that indicated by examination order information. There may be a case where imaging last time was performed in a manner different from that indicated by examination order information last time, but the technician this time is unaware of that. Then, the controller 21 may compare the determination result of the failed-image determination process about positioning about the previous radiograph with the determination result of the failed-image determination process about positioning about the current radiograph, and determine whether the current radiograph is a failed image. This can reinforce determination as to whether positioning is good (whether radiographs are failed images) on the basis of previous radiographs.

Further, in the above, the computer readable storage medium storing the programs of the present disclosure is a hard disk, a nonvolatile semiconductor memory or the like, but not limited thereto and may be a portable recording medium, such as CD-ROM. Further, as a medium to provide data of the programs of the present disclosure via a communication line, a carrier wave can be used.

Although one or more embodiments of the present invention have been described and illustrated in detail, the disclosed embodiments are made for purposes of not limitation but illustration and example only. The scope of the present invention should be interpreted by terms of the appended claims.

What is claimed is:

1. A failed-image decision support apparatus comprising:
    a hardware processor that performs, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
    an outputter that outputs the determination result and the determination basis information.

2. The failed-image decision support apparatus according to claim 1, wherein the determination result is generated by analyzing the medical image in the failed-image determination process.

3. The failed-image decision support apparatus according to claim 1, wherein the outputter comprises a display.

4. The failed-image decision support apparatus according to claim 3, wherein the display displays the determination basis information in at least one of a form of textual information and a form of a marker laid and displayed on the medical image.

5. The failed-image decision support apparatus according to claim 3, wherein the determination basis information includes information indicating at least one of a type of the failed-image determination process performed to generate the determination result, a numerical value obtained by analyzing the medical image in the failed-image determination process and used to generate the determination result, and a marker laid on a region in the medical image used to generate the determination result in the failed-image determination process.

6. The failed-image decision support apparatus according to claim 4, further comprising a switch that toggles the marker between displaying and hiding, in a case in which the marker is displayed on the medical image.

7. The failed-image decision support apparatus according to claim 4, wherein in a case in which the marker is displayed on the medical image, the hardware processor performs control to hide the marker displayed on the medical image while an operation for image processing is being made for the medical image displayed by the display.

8. The failed-image decision support apparatus according to claim 4, wherein after an operation to change at least one of a shape, a size, and a position of the medical image displayed by the display is made, the hardware processor performs control such that the marker is displayed following the change in the medical image.

9. The failed-image decision support apparatus according to claim 8, wherein the hardware processor performs control such that the marker is displayed following the change in the medical image while the operation to change the at least one of the shape, the size, and the position of the medical image displayed by the display is being made.

10. The failed-image decision support apparatus according to claim 1, wherein the processor is configured to display, as the determination basis information, a marker which is attached to and superposed on a region in the medical image, which region is used to generate the determination result in the failed-image determination process.

11. A failed-image decision support apparatus comprising a hardware processor that:
performs, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
controls output of the determination result and the determination basis information.

12. A failed-image decision support system comprising:
a hardware processor that performs, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
an outputter that outputs the determination result and the determination basis information.

13. A failed-image decision support system comprising a hardware processor that:
performs, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
controls output of the determination result and the determination basis information.

14. A failed-image decision support method comprising:
performing, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
outputting the determination result and the determination basis information.

15. A failed-image decision support method comprising:
performing, from among multiple types of failed-image determination processes, at least one failed-image determination process on a medical image, the failed-image determination process being a process using an inference obtained by a learned model to thereby generate (i) a determination result and (li) determination basis information indicating a basis for the determination result; and
controlling output of the determination result and the determination basis information.

16. A non-transitory computer readable storage medium storing a program that causes a computer to:
perform, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
output the determination result and the determination basis information.

17. A non-transitory computer readable storage medium storing a program that causes a computer to:
perform, from among multiple types of failed-image determination processes, at least one failed-image determination process on a medical image, the failed-image determination process being a process using an inference obtained by a learned model to thereby generate (i) a determination result and (ii) determination basis information indicating a basis for the determination result; and
control output of the determination result and the determination basis information.

* * * * *